United States Patent

Fujii et al.

Patent Number: 5,521,180
Date of Patent: May 28, 1996

[54] MORPHOLINE DERIVATIVE

[75] Inventors: Mitsuo Fujii; Takayuki Suzuki, both of Ibaraki; Satoshi Hayashibe, Tokyo; Shin-ichi Tsukamoto; Shin-ichi Yatsugi, both of Ibaraki; Tokio Yamaguchi, Saitama, all of Japan

[73] Assignee: Yamanouchi Pharmaceutical Co., Ltd., Tokyo, Japan

[21] Appl. No.: 495,619

[22] PCT Filed: Feb. 8, 1994

[86] PCT No.: PCT/JP94/00186

§ 371 Date: Aug. 3, 1995

§ 102(e) Date: Aug. 3, 1995

[87] PCT Pub. No.: WO94/18182

PCT Pub. Date: Aug. 18, 1994

[30] Foreign Application Priority Data

Feb. 10, 1993 [JP] Japan .................................. 5-045691
Sep. 27, 1993 [JP] Japan .................................. 5-240147

[51] Int. Cl.$^6$ ...................... A61K 31/535; C07D 265/30
[52] U.S. Cl. ........................................ 514/239.2; 544/174
[58] Field of Search ........................ 544/174; 514/239.2

[56] References Cited

U.S. PATENT DOCUMENTS 3,714,161  1/1973  Blakeney et al. ........................ 544/174

*Primary Examiner*—Robert W. Ramsuer
*Attorney, Agent, or Firm*—Sughrue, Mion, Zinn, Macpeak & Seas

[57] ABSTRACT

A morpholine derivative represented by formula (I) or a pharmaceutically acceptable salt thereof:

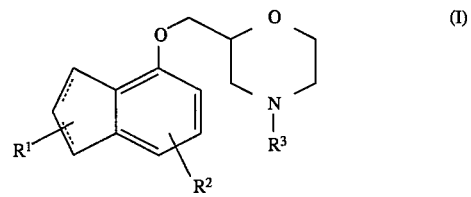

wherein $R^1$ and $R^3$, which may be the same or different, each represent a hydrogen atom or a lower alkyl group; $R^2$ represents a halogen atom; and the dotted line indicates an optional double bond.

These compounds exhibit a selective 5-HT reuptake inhibitory activity and a selective 5-HT$_2$ receptor antagonistic activity and useful as a therapeutic agent for depression, anxiety, etc. with reduced side effects.

10 Claims, No Drawings

MORPHOLINE DERIVATIVE

This application is a 371 of PCT/JP94/00186 filed Feb. 8, 1994.

TECHNICAL FIELD

This invention relates to a morpholine derivative or a salt thereof having an antidepressive activity and an antianxiety activity.

BACKGROUND ART

Participation of serotonin (hereinafter referred to as 5-HT) in antidepressive action has been reported [Norio Ogawa (ed.), Shinnonoreseputa, Sekai Hoken Tsushinsha (1991, etc.)], and studies have been directed to 5-HT reuptake inhibition or action on 5-HT receptors.

Tricyclic compounds such as Amitriptyline are widely used clinically as antidepressants. Although Amitriptyline exhibits a 5-HT reuptake inhibitory activity or a 5-$HT_2$ receptor antagonistic activity, it additionally has a noradrenaline reuptake inhibitory activity and an anticholine activity and exhibits non-selective action and is therefore considered to cause side effects upon the cardiovascular system (e.g., palpitation), thirst, urinary retention, etc. Therefore, drugs which selectively inhibit 5-HT reuptake or selectively act on 5-$HT_2$ receptors are expected to have reduced side effects. Drugs selectively inhibitory on 5-HT reincorporation which have been clinically used include, for example, Fluoxetine. However, it has been reported that Fluoxetine induces anxiety or insomnia during the course of therapy [*Physician's Desk Reference*, Medical Economics Company, Oradell, N.J. (1990)].

Drugs which selectively antagonize for 5-$HT_2$ receptors include, for example, Mianserin which is known as an antidepressive.

In the latest various studies, a compound having a selective 5-HT reuptake inhibitory activity together with a selective 5-$HT_2$ receptor antagonistic activity is eagerly awaited [*Cell Biology to Pharmacology and Therapeutics*, 488–504 (1990), *Psychopathology*, 22 (suppl. 1), 22–36 (1989), *J. Clin. Psychiatry*, 52, 34–38 (1991), *Psychopharmacol. Bull.*, 26, 168–171 (1990), and *Br. J. Pharmacolo.*, 100, 793–799 (1990)].

Drugs having both of a 5-HT reuptake inhibitory activity and a 5-$HT_2$ receptor antagonistic activity include, for example, Trazodone. However, the 5-HT reuptake inhibitory activity of Trazodone is very weak, and it was reported that the antidepressive activity and antianxiety activity of Trazodone are based on its antagonism for 5-$HT_2$ receptors. [Marek G. J., et al., *Psychopharmacology*, 109, 2–11 (1992)]. Further, in addition to the above two activities Trazodone also exhibits affinity to $\alpha_1$ receptors and therefore causes sides effects based thereon.

JP-A-46-7333 (the term "JP-A" means an "unexamined published Japanese patent application") discloses 2-[[(4-indanyl)oxy] methyl]morpholine, and JP-A-52-83773 discloses 2-[[(7-indenyl)oxy]methyl]morpholine. However, these compounds have no substituent on the indanyloxy group or indenyloxy group thereof.

DISCLOSURE OF THE INVENTION

The present invention relates to a morpholine derivative which is structurally characterized by its halogen atom on the benzene ring of an indanyloxy group or an indenyloxy group and therefore quite different in chemical structure from the conventional compounds.

The morpholine derivative of the present invention exhibits a selective 5-HT reuptake inhibitory activity and a selective 5-$HT_2$ receptor antagonistic activity, both the activities produce excellent effects.

An object of the present invention is to provide a novel morpholine derivative represented by the formula (I) shown below or a salt thereof.

Another object of the present invention is to provide a medicine having a selective 5-HT reuptake inhibitory activity together with a selective 5-$HT_2$ receptor antagonistic activity which comprises as an active ingredient the compound (I) of the present invention or a salt thereof and to provide a pharmaceutical composition comprising the compound (I) of the present invention or a salt thereof and a pharmaceutically acceptable carrier.

The present invention includes in its scope a compound represented by the formula (II) shown below, which is included in the compound (I) of the present invention, or a salt thereof and, therefore, a further object of the present invention is to provide the compound (II).

1) Morpholine derivative represented by the formula (I) and a salt thereof:

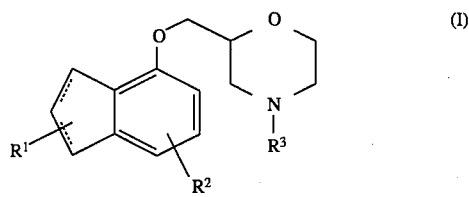

wherein $R^1$ and $R^3$, which may be the same or different, each represent a hydrogen atom or a lower alkyl group; $R^2$ represents a halogen atom; and the dotted line may indicate an optional double bond.

2) Morpholine derivative represented by the formula (II) or a salt thereof:

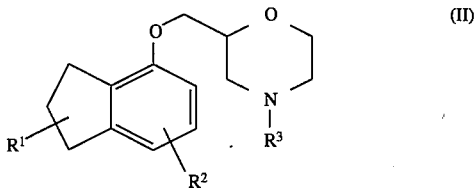

wherein $R^1$ and $R^3$, which may be the same or different, each represent a hydrogen atom or a lower alkyl group; and $R^2$ represents a halogen atom.

The compounds of the present invention are described below in more detail. Unless otherwise indicated, the terminology "lower" as used in the definitions for general formulae denotes a straight or branched carbon chain containing 1 to 6 carbon atoms.

Specific examples of the "lower alkyl group" are methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups.

A lower alkyl group having 1 to 3 carbon atoms, such as methyl, ethyl, propyl or isopropyl group, is preferred.

The "halogen atom" includes a fluorine atom, a chlorine atom, a bromine atom, and an iodine atom, with a fluorine atom being preferred.

The dotted line means that the indane ring may have a double bond. That is, according to the meaning of the dotted line, examples of the structure of formula (I):

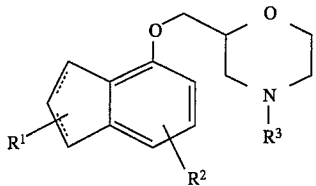

are each of the following formulae:

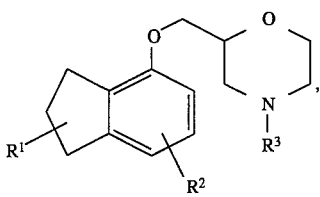

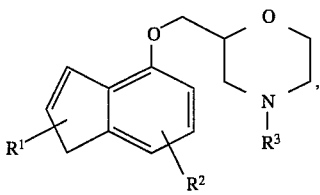

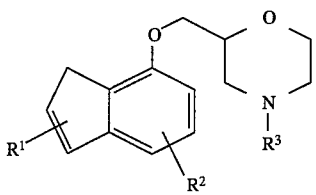

wherein the symbols are as defined above, or a mixture of compounds (a) and (b).

Depending on the 2-position of the morphonyl group or the kind of the substituent, the compounds of the present invention include stereoisomers such as optical isomers based on an asymmetric carbon atom and geometrical isomers. The present invention is to include all these isomers either as a mixture or as isolated. Preferred of the isomers of compounds (I) and (II) or salts thereof are levorotatory optical isomers.

The compounds (I) and (II) may form salts with acids. Such salts includes acid addition salts with inorganic acids, for example, mineral acids such as hydrochloric acid, hydrobromic acid, hydroiodic acid, sulfuric acid, nitric acid, and phosphoric acid; or with organic acids, such as formic acid, acetic acid, propionic acid, oxalic acid, malonic acid, succinic acid, fumaric acid, maleic acid, lactic acid, malic acid, citric acid, tartaric acid, D-dibenzoyltartaric acid, carbonic acid, picric acid, methanesulfonic acid, ethanesulfonic acid, and glutamic acid. Hydrochlorides, oxalates, fumarates, and D-dibenzoyltartrates are preferred.

The compounds of the present invention can form hydrates and various solvates or show polymorphism.

Process for Preparation:

The compounds of the present invention may be prepared by the following processes, but the process for preparing the compounds is not limited thereto.

Process 1:

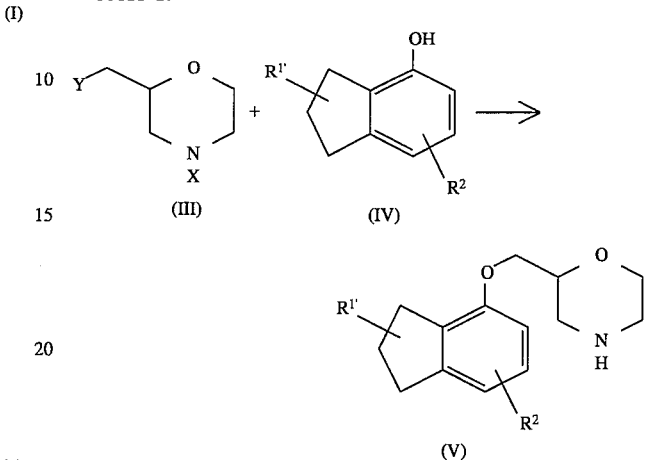

wherein $R^2$ is as defined above; $R^{1'}$ represents a hydrogen atom, a lower alkyl group or a ketone group; X represents an amino protective group; and Y represents a halogen atom, a mesyloxy group or a tosyloxy group.

The amino protective group is a commonly employed protective group and includes a trityl group, a benzhydryl group, a p-methoxybenzyl group, and a tert-butyl group, with a trityl group being preferred.

The above reaction is carried out by stirring the morpholine compound (III) and the indanol compound (IV) at a reaction corresponding ratio in an inert solvent in the presence of a base at room temperature or under heating, or the indanol compound (IV) is previously converted to its sodium or potassium salt and then reacted with the morpholine compound (III) in an inert solvent at room temperature or under heating (step 1). The protective group of the product is released in a usual manner by, for example, reduction (e.g., catalytic reduction, reduction with liquid ammonia, etc.) or treatment with an acid, to obtain the compound (V) of the present invention (step 2). The inert solvent to be used in step 1 includes benzene, chloroform, dimethylformamide (hereinafter abbreviated as DMF), dimethyl sulfoxide (hereinafter abbreviated as DMSO), ethyl ether, water, methanol, and ethanol. The base to be used in step 1 includes sodium hydroxide, potassium hydroxide, sodium hydride, potassium hydride, lithium hydride, potassium carbonate, sodium carbonate, butyl lithium, and potassium tert-butoxide. The acid to be used in step 2 includes acetic acid, trifluoroacetic acid, trichloroacetic acid, hydrochloric acid, sulfuric acid, and hydrobromic acid-acetic acid. The reaction for removal of a protective group is usually effected in an inert solvent, such as methanol, ethanol or acetone, or in water at room temperature or under heating (under reflux).

Process 2:

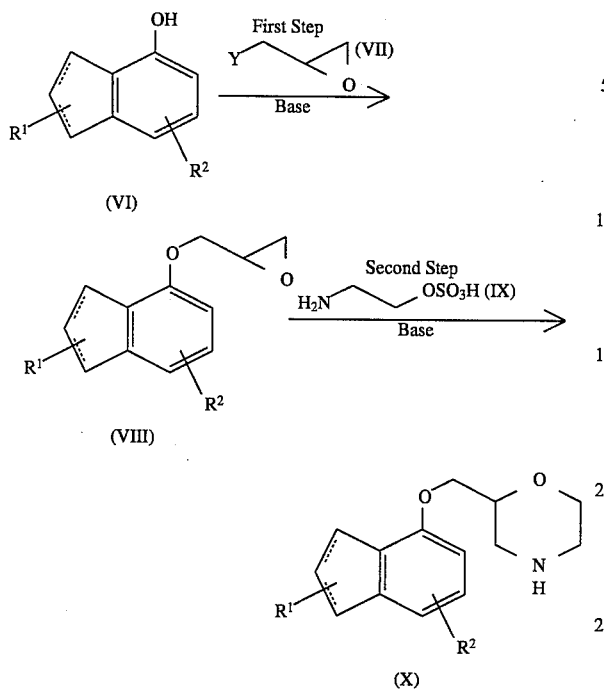

wherein $R^1$, $R^2$, Y, and the dotted line are as defined above.

Step 1: Synthesis of halogeno-4-indanyl(or indenyl) glycidyl ether

The halogeno-4-indanyl(or indenyl) glycidyl ether (VIII) can be synthesized by reacting the indanol (or indenol) compound (VI) and the propylene oxide compound (VII) in a solvent, such as water, acetone or acetonitrile, in the presence of a base, such as sodium hydroxide, potassium hydroxide or potassium carbonate, under a condition of from 0° C. to heat refluxing. Step 2: Synthesis of 2-[[halogeno-4-indanyl(or indenyl)oxy]methyl]morpholine The 2-[[(halogeno-4-indanyl(or indenyl)oxy]methyl]morpholine (X) can be synthesized by reacting the halogeno-4-indanyl(or indenyl) glycidyl ether (VIII) and the aminoethylsulfuric acid (IX) in a mixed solvent, such as water-methanol or water-ethanol, in the presence of a base, such as sodium hydroxide or potassium hydroxide, under a condition of from 0° C. to heat refluxing.

The thus prepared compound (X) of the present invention may be converted to a salt with an acid, such as hydrochloric acid, fumaric acid, succinic acid, oxalic acid, D-dibenzoyltartaric acid, etc.

In the processes 1 and 2, where the optically active morpholine compound (III) or the optically active propylene oxide compound (VII) is used, a corresponding optically active 2-[[(halogeno-4-indanyl(or indenyl))oxy]methyl]morpholine can be obtained.

The compound obtained by the processes 1 to 5 can be purified to have an increased optical purity by the recrystallization using D-dibenzoyltartaric acid, D-ditoluoyltartaric acid, D-tartaric acid, etc. as a resolving agent and acetonitrile-water, methanol, dimethylformamide, etc. as a recrystallizing solvent.

Process 3:

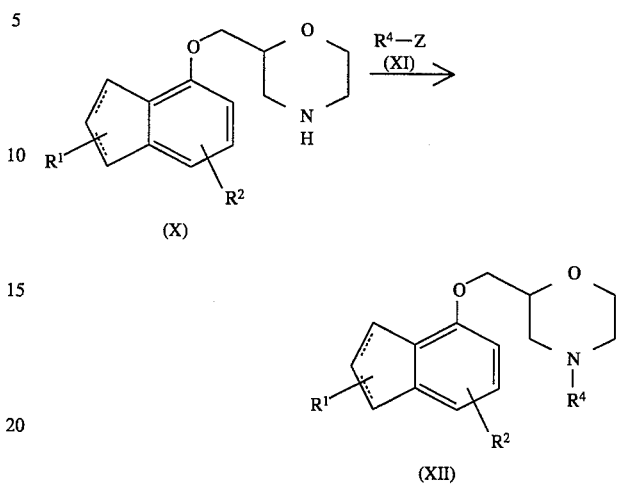

wherein $R^1$, $R^2$, and the dotted line are as defined above; $R^4$ represents the lower alkyl group of $R_3$; and Z represents a halogen atom, an arylsulfonyloxy group, a lower alkylsulfonyloxy group or an alkyl sulfate group.

The arylsulfonyloxy group includes a phenylsulfonyloxy group and a p-toluenesulfonyloxy group; the lower alkylsulfonyloxy group includes a methylsulfonyloxy group, an ethylsulfonyloxy group, and a propylsulfonyloxy group; and the alkyl sulfate group includes a methyl sulfate group, an ethyl sulfate group, and a propyl sulfate group.

The compounds of the present invention may be obtained through N-alkylation in a conventional manner.

The N-alkylation is carried out by reacting the unsubstituted morpholino compound (X) with a reaction corresponding amount of alkylating agent (XI) in an inert solvent, such as acetone, acetonitrile, tetrahydrofuran (hereinafter abbreviated as THF), ethyl ether or DMF, in the presence of a base, such as potassium carbonate, sodiumhydride or potassium hydride, at room temperature to a heating temperature (or under reflux).

(Alternative Process)

Alternatively, N-alkylation can be carried out by stirring the unsubstituted morpholino compound (X) in the presence of a reaction corresponding amount of a lower alkylaldehyde and sodium borohydride, sodium triacetoxyborohydride, sodium cyanoborohydride, etc. in an inert solvent, such as methanol, ethanol, THF or dioxane, at room temperature or a heating temperature. This reaction is preferably conducted under an acidic condition by addition of hydrochloric acid, acetic acid, formic acid, etc.

Process 4:

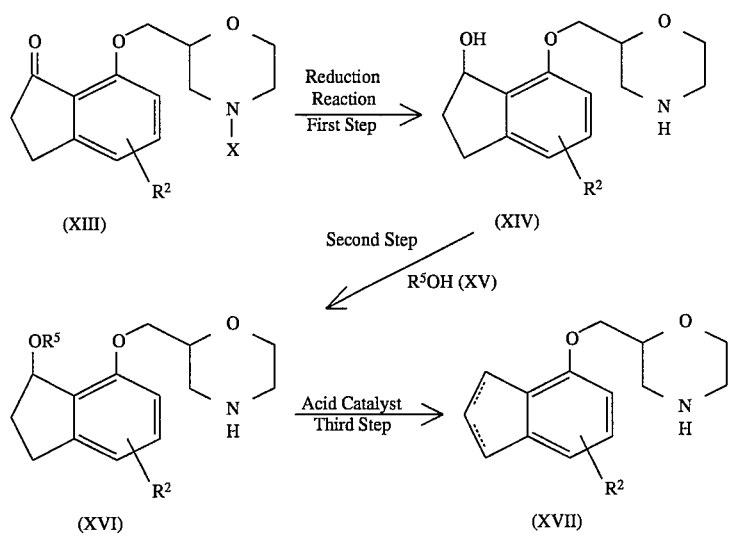

wherein $R^2$, X, and the dotted line are as defined above; and $R^5$ represents a lower alkyl group.

The lower alkyl group as $R^5$ is as mentioned above and is preferably a methyl group or an ethyl group.

The indene compound (XVII) of the present invention can be obtained through the following steps.

Step 1:

Step 1 is based on the conventional reduction. Typical reaction modes are shown below.

Process A:

The ketone compound (XIII) is reacted with a reaction corresponding amount of a reducing agent (e.g., borane, alane, sodium tetrahydroboron, lithium tetrahydroboron, lithium tetrahydroaluminum, sodium triacetoxyborohydride, diisobutyl aluminum hydride or sodium cyanoboron) in an inert solvent, such as a lower alcohol (e.g., methanol, ethanol or propanol), diethyl ether, THF, benzene, toluene, dichloroethane, chloroform or water), while cooling to heating under reflux to obtain the hydroxy compound (XIV).

Process B (catalytic reduction):

The ketone compound (XIII) is stirred with a metallic catalyst (e.g., Raney nickel, nickel or dichlorocopper tetroxide) in an alcohol, such as methanol or ethanol, at room temperature to a heating temperature.

Process C:

The ketone compound (XIII) and a reaction corresponding amount of a dithionite (e.g., sodium dithionite) are stirred in a mixed solvent, such as DMF-water, THF-water, dioxane-water, methanol-water or ethanol-water, while cooling or at room temperature.

Step 2:

The reaction is carried out by stirring the hydroxy compound (XIV) in the alcohol (XV), such as methanol or ethanol, under an acidic condition with hydrochloric acid, acetic acid, trifluoroacetic acid, trichloroacetic acid, sulfuric acid or hydrobromic acid-acetic acid, at room temperature or under heating.

Step 3:

The reaction is carried out by stirring the alkoxy compound (XVI) obtained in the step 2 in an inert solvent, such as toluene, benzene, THF or 1,4-dioxane, in the presence of an acid catalyst (e.g., hydrochloric acid, sulfuric acid, phosphoric acid, p-toluenesulfonic acid or acetic acid) at room temperature or under heating.

The 2-[[(halogeno-4-indenyl)oxy]methyl]morpholine derivative or 2-[[(halogeno-7-indenyl)oxy]methyl]morpholine derivative obtained by the processes 1 to 4 is in some cases partly isomerized with ease at room temperature to give an approximately 1:1 isomeric mixture.

The mixture can be separated into each isomers by converting the compound to an addition salt through a conventional salt-forming reaction followed by separation by, for example, recrystallization.

Process 5:

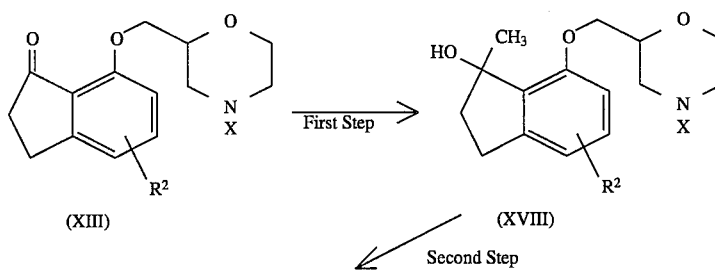

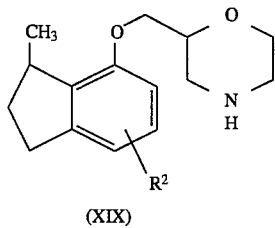

(XIX)

wherein R² and X are as defined above.

This process is to obtain the compound (XIX) of the present invention, in which the 3-position of the indane ring is substituted with a methyl group. Step 1:

The reaction is carried out by reacting the ketone compound (XIII) and a reaction corresponding amount of a methylating agent, such as an organometallic reagent (e.g., methyllithium, Grignard reagent, a methyl halide, trimethylaluminum, methylcopper or dimethylcopper) in an anhydrous solvent, such as THF, diethyl ether, benzene, toluene, dichloromethane or 1,4-dioxane, while cooling or at room temperature.

In a preferred reaction mode, the ketone compound (XIII) and a reaction corresponding amount of methyllithium or methylmagnesium bromide are stirred in THF or diethyl ether under cooling or at room temperature, e.g., from −78° to 0° C.

Step 2 (reduction):

Process A:

The hydroxymethyl compound (XVIII) obtained in the step 1 is catalytically reduced in a conventional manner. The reaction is typically conducted by stirring the compound (XVIII) in an inert solvent, such as a lower alcohol (e.g., methanol, ethanol or propanol), THF, 1,4-dioxane, diethyl ether, ethyl acetate, benzene, toluene or dichloromethane, in the presence of a metallic catalyst (e.g., palladium-on-carbon, dihydroxypalladium or platinum dioxide) in a hydrogen atmosphere while cooling or at room temperature.

Process B:

The hydroxymethyl compound (XVIII) obtained in the step 1 and a reaction corresponding amount of a trialkylsilane (e.g., trimethylsilane or triethylsilane) are stirred in an inert solvent, such as methanol, ethanol, THF, dioxane, diethyl ether or acetonitrile, in the presence of an acid, such as acetic acid, trifluoroacetic acid, hydrochloric acid, hydrobromic acid, sulfuric acid or phosphoric acid, while cooling with ice or at room temperature.

(Alternative process of Process 5)

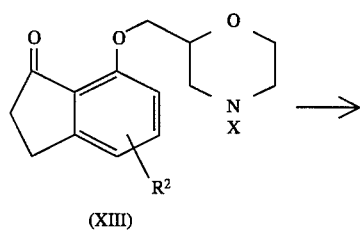

(XIII)

-continued
(Alternative process of Process 5)

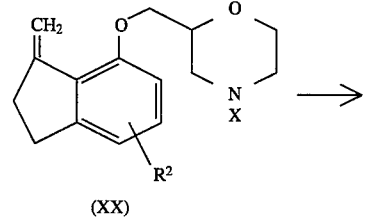

(XX)

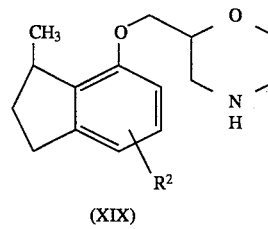

(XIX)

wherein R² and X are as defined above.

The reaction is performed by subjecting the ketone compound (XIII) to the usual Wittig reaction using a Wittig reagent (e.g., CH₂PPh₃) in a conventional manner [Shin Jikken Kagaku Koza 14(I), 224–238, Maruzen K.K. (1977)] to obtain the exo-methylene compound (XX) (step 1). The exo-methylene compound (XX) obtained in the step 1 is then reduced in a conventional manner [*Reductions in Organic Chemistry*, Ellis Horwood Ltd. (1984)].

INDUSTRIAL APPLICABILITY

The compound of the present invention inhibits reuptake of 5-HT with high selectivity and also exhibits selective antagonism for 5-HT₂ receptors. Therefore, the compound is useful as a therapeutic agent for depression, anxiety, psychosomatic diseases, autonomic imbalance or anxiety petition with reduced side effects and a therapeutic agent for marginal involvement associated with cerebrovascular disturbances or Alzheimer disease, such as spontaneity reduction, dysthymia, anxiety and impatience, hallucination and illusion, hypochondria, disorder of sleep, and the like. Further, the compound of the present invention has the anti-reserpine action, blood viscosity improving action, antihypoxic action, and antioxidation and is useful as an agent for cerebral circulation and metabolism improvement or an agent for cerebral function improvement and is also useful as an analgesic. Furthermore, the compound of the present invention can be used for the improvement of cerebral dysfunction or dementia accompanying Alzheimer disease.

A test of 5-HT reuptake inhibition and a test of 5-HT₂ receptor antagonism for demonstrating the effects of the compound of the present invention are described below in detail.

1) Test on 5-HT Reuptake Inhibition in vitro Test:

The 5-HT reuptake inhibitory activity was tested by examining the degree of inhibition of a test compound on binding of [$^3$H]-Citalopram to 5-HT reuptake sites.

The method of D'amato RJ, et al. described in *J. Pharmacol. Exp. Ther.*, 242, 364 (1987) was used. A buffer solution (0.5 ml) containing about 1.0 nM of [$^3$H]-Citalopram, a rat cerebral cortex membrane preparation (about 0.4 mg-protein), and a test compound was allowed to react at 25° C. for 60 minutes. Thereafter, the labeled ligand of bound form was separated form the labeled ligand of free form by suction filtration. The amount of the ligand nonspecifically bound to the 5-HT reuptake sites, which was obtained by adding excess non-labeled Fluoxetine (10 μM), was subtracted from the total amount of the bound ligand to obtain the amount of the ligand specifically bound to the 5-HT reuptake sites. The IC$_{50}$ (the concentration which reduces the amount of the specifically bound ligand by 50%) for each compound was calculated and converted to a dissociation constant (Ki value). in vivo Test:

Enhancement of the action of L-5-hydroxytryptophan which is a 5-HT precursor was tested [*Naunyn-Schmiedeberg's Archives of Pharmacology*, 311, 185–192 (1980)]. Male ICR mice weighing from 30 to 40 g were used. A test drug was intraperitoneally administered, and 30 minutes later 90 mg/kg of L-5-hydroxytryptophan was intravenously injected. After 5 minutes from the injection, the animals were observed for 5 minutes in terms of tremor, head shaking behavior, and hind leg abduction. The test drug was evaluated from the ED$_{50}$ in manifestation of each action.

2) Test on Selectivity in 5-HT Reuptake Inhibition

The degree of inhibition of a test compound on uptake of [$^3$H]-5-HT, [$^3$H]-noradrenaline and [$^3$H]-dopamine into synaptosomes was examined. The method of Harada and Maeno described in *Biochem. Pharmacol.*, 28, 2645 (1979) was used. A Wistar male rat was decapitated and the cerebral cortex and the corpus striatum were taken out. The synaptosome fraction of the cerebral cortex was prepared for 5-HT and noradrenaline uptake and that of the corpus striatum was prepared for dopamine uptake. Each synaptosome fraction was incubated at 37° C. for 3 minutes, and [$^3$H]-5-HT, [$^3$H]-noradrenaline and [$^3$H]-dopamine (10$^{-7}$M) was added to the respective fraction. After further incubation for 2 minutes, the system was cooled with ice (0° C.) to stop the reaction. Then, the reaction system was filtered through a Whatman CF/B glass filter, and the radioactivity trapped on the filter was measured with a liquid scintillation counter. The nonspecific activity was obtained by using a reaction system containing no test drug and having been incubated at 0° C. The test drug was evaluated from the IC$_{50}$ (the concentration at which the uptake of each radioactive ligand reduced by 50%).

3) Test on Antagonism for 5-HT$_2$ Receptors (in vitro):

The degree of inhibition of a test compound on binding of [$^3$H]-Ketanserin was tested. The method of Leysen JE, et al. described in *Mol. Pharmacol.*, 21, 301 (1982) was used. A buffer solution (0.5 ml in total) containing about 1.0 nM of [$^3$H]-Ketanserin, a rat cerebral cortex membrane preparation (about 0.2 mg-protein), and a test compound was allowed to react at 25° C. for 30 minutes. Thereafter, the bound labeled ligand was separated by suction filtration. The amount of the ligand nonspecifically bound to the 5-HT$_2$ receptors, which was obtained by adding excess non-labeled Metergoline (10 μM), was subtracted from the total amount of the bound ligand to obtain the amount of the ligand specifically bound to 5-HT$_2$ receptors. The IC$_{50}$ (the concentration at which the amount of the specifically bound ligand is reduced by 50%) for each compound was calculated and converted to a dissociation constant (Ki value).

(Test Results)

The above tests proved that the compound of the present invention possesses both a 5-HT reuptake inhibitory activity and a 5-HT$_2$ receptor antagonistic activity in vitro and both the activities produce excellent effects. To the contrary, the comparative compounds used showed very weak 5-HT$_2$ receptor antagonism, while exhibiting a 5-HT reincorporation inhibitory activity (see Table 1 below).

TABLE 1

| Test Compound | Inhibition on 5-HT reuptake (Ki Value) | Antagonism for 5-HT$_2$ Receptor (Ki Value) |
| --- | --- | --- |
| Example 4 | 21 nM | 100 nM |
| Example 5 | 21 nM | 100 nM |
| Comparative Compound 1 | 52 nM | 1032 nM |
| Comparative Compound 2 | 22 nM | 4675 nM |

Note:
Comparative compound 1:
2-[[(4-Indanyl)oxy]methyl]morpholine (the compound described in JP-A-46-7333)
Comparative compound 2:
2-[[(7-Indenyl)oxy]methyl]morpholine (the compound described in JP-A-52-83773)

Note:
Comparative compound 1:
2-[[(4-Indanyl)oxy]methyl]morpholine (the compound described in JP-A-46-7333)
Comparative compound 2:
2-[[(7-Indenyl)oxy]methyl]morpholine (the compound described in JP-A-52-83773)

Further, in the in vivo test on 5-HT reuptake inhibition, the ED$_{50}$ of the compound of, for example, Example 4 in manifestation of tremor, head shaking behavior, and hind leg abduction was 6.3 mg/kg, 7.2 mg/kg and 14.1 mg/kg, respectively, indicating a powerful inhibitory activity on 5-HT reuptake.

In the test on selective 5-HT reuptake inhibition, the IC$_{50}$ of the compound of, for example, Example 1 in inhibition of [$^3$H]-5-HT uptake, [$^3$H]-noradrenaline uptake and [$^3$H]-dopamine uptake was 227 nM, 6722 nM and 10000 nM or more, respectively. These results reveal that the [$^3$H]-5-HT uptake inhibitory activity of the compound of Example 1 is about 30 or more times the [$^3$H]-noradrenaline uptake inhibitory activity and the [$^3$H]-dopamine uptake inhibitory activity and, therefore, shows selectivity to 5-HT uptake.

Accordingly, the compound of the present invention is expected to cause no side effect observed with compounds having nonselective uptake inhibitory activities, such as side effects on the cardiovascular system (e.g., palpitation), and other side effects such as thirst and urinary-retention.

Preparations containing at least one of the compound of the present invention or a salt thereof as an active ingredient may be prepared by using carriers, vehicles and other additives generally employed in pharmaceutical preparations.

The carriers or vehicles to be used in preparations may be either solid or liquid and include lactose, magnesium stearate, starch, talc, gelatin, agar, pectin, gum arabic, olive oil, sesame oil, cacao butter, ethylene glycol and others for common use.

The compound of the present invention can be administered either orally in the dosage form of tablets, pills, capsules, granules, powders, liquids, etc., or parenterally in the dosage form of injections for, for example, intravenous or intramuscular administration, suppositories or preparations for transdermal administration.

The dose generally ranges from 1 to 1000 mg, preferably 10 to 300 mg, per day for adults, usually given in a single or several divided doses, while varying depending on the age, body weight and conditions of patients, the therapeutic effect, the administration route, the period of treatment, and the like. As a matter of course, lower doses may be sufficient in some cases since the dose may vary with various conditions as mentioned above.

BEST EMBODIMENT FOR CARRYING OUT THE INVENTION

The present invention will now be illustrated in greater detail with reference to Examples, but it should be understood that the present invention should not be construed as being limited thereto.

Preparation of the starting compounds used in Examples is explained by way of Reference Examples.

The chemical structures of the compounds obtained in Examples are shown in Tables 2 through 4.

REFERENCE EXAMPLE 1

(i) Aminoethyl sulfate (423.6 g, 3.00 mol) was dissolved in a 70% aqueous solution of sodium hydroxide (360 ml), and a methanol solution (400 ml) of allyl glycidyl ether (68.4 mg, 0.60 mol) was added thereto dropwise at 50° C. After stirring the mixture at that temperature for 1 hour, a 70% aqueous solution of sodium hydroxide (600 ml) was added thereto, followed by stirring at the same temperature for 13 hours.

After completion of the reaction, water was added to the reaction mixture at room temperature, and the mixture was extracted with chloroform (6×1000 ml). The extract was washed with a saturated aqueous solution of sodium chloride (2×200 ml) and dried over magnesium sulfate. The solvent was removed by evaporation, and the residue was subjected to distillation under reduced pressure to give 2-(allyloxymethyl)morpholine (75.2 g) as a colorless oily substance.
Physicochemical Properties:
$^1$H-NMR (CDCl$_3$) δ: 2.65 (dd, J=10.3 Hz, J=12.2 Hz, 1H), 2.74–2.93 (m, 3H), 3.36–3.49 (m, 2H), 3.59–3.70 (m, 2H), 3.90 (dd, J=1.96 Hz, J=11.7 Hz, 1H), 4.01 (dd, J=0.96 Hz, 5.84 Hz, 2H, 9-H), 5.17–5.25 (m, 1H, 11-H), 5.28–5.30 (m, 1H, 11-H), 5.86–5.96 (m, 1H, 10-H)
MS (GC/MS): m/z 157 (M$^+$)

(ii) 2-(Allyloxymethyl)morpholine (39.5 g, 0.25 mol) was dissolved in 1,4-dioxane (500 ml), and potassium tert-butoxide (28.2 g, 0.25 mol) was added to the solution at room temperature, followed by heating under reflux for 3 hours. After completion of the reaction, water was added to the reaction mixture at room temperature, and the reaction mixture was extracted with chloroform (3×1000 ml). The extract was washed with a saturated aqueous solution of sodium chloride (1000 ml) and dried over magnesium sulfate. The solvent was evaporated to give crude 2-(1-propenyloxymethyl)morpholine (40.0 g) as a pale yellow oily substance.
Physicochemical Properties:
$^1$H-NMR (CDCl$_3$) δ: 1.58 (dd, J=1.80 Hz, J=6.84 Hz, 3H, 10-H), 2.75–2.92 (m, 2H), 3.46–4.10 (m, 7H), 4.42 (dq, J=1.70 Hz, J=6.57 Hz, 1H), 5.96 (dq, J=1.70 Hz, 6.21 Hz, 1H)
MS (GC/MS): m/z 157 (M$^+$)

(iii) The crude 2-(1-propenyloxymethyl)morpholine (32.7 g) was dissolved in an acetone-water (9:1) mixed solvent containing 2.0N hydrochloric acid, followed by heating under reflux for 4 hours. After completion of the reaction, the solvent was evaporated to obtain a crude alcohol compound (41.8 g) as a pale yellow oily substance. Triethylamine (145 ml) was added dropwise to a methylene chloride solution (300 ml) of the crude alcohol compound (41.8 g) under ice-cooling, and triphenylchloromethane (41.5 g, 0.208 mol) was added thereto at the same temperature, followed by stirring for 2 hours. After completion of the reaction, a saturated aqueous solution of sodium hydrogencarbonate (150 ml) was added to the reaction mixture, and the mixture was extracted with chloroform. The extract was dried over magnesium sulfate, the solvent evaporated, and the residue recrystallized from methylene chloride-hexane to give 2-hydroxymethyl-4-tritylmorpholine (48.0 g).
Physicochemical Properties:
IR (KBr): 3450 cm$^{-1}$
$^1$H-NMR (CDCl$_3$) δ: 1.12–1.90 (m, 2H), 2.80–2.98 (m, 2H), 3.28–3.56 (m, 3H), 3.80–4.05 (m, 3H), 7.06–7.58 (m, 15H, C(C$_6$H$_5$)$_3$)
MS (FAB/pos.): m/z 360 [(M+1)$^+$]

(iv) Pyridine (20.3 ml, 0.251 mol) was added dropwise to a methylene chloride solution (100 ml) of the trityl compound (15.0 g) under ice-cooling, and a methylene chloride solution (100 ml) of p-toluenesulfonyl chloride (15.9 g) was added thereto dropwise at the same temperature, followed by stirring for 13 hours. After completion of the reaction, a saturated aqueous solution of sodium hydrogencarbonate was added under ice-cooling, followed by extraction with chloroform. The extract was washed with a saturated aqueous solution of sodium chloride and dried over magnesium sulfate. The solvent was evaporated, and the residue was recrystallized from 1,2-dichloroethane to give 2-p-toluenesulfonyloxymethyl-4-tritylmorpholine (14.0 g).
Physicochemical Properties:
IR (KBr): 1730 cm$^{-1}$
$^1$H-NMR (CDCl$_3$) δ: 1.34–1.70 (m, 2H), 2.43 (s, 3H, PhCH$_3$), 2.75–2.94 (m, 2H), 3.72–4.04 (m, 5H), 7.10–7.40 (m, 17H), 7.70 (d, J=2.10 Hz, 2H)
MS (FAB/pos.): m/z 514 [(M+1)$^+$]

REFERENCE EXAMPLE 2

(i) Phenol (8.00 g) was added to a mixed solution of an aqueous solution (50 ml) of sodium hydroxide (3.43 g) and methylene chloride (60 ml) at room temperature. Then, tetrabutylammonium hydrogensulfate (0.48 g) was added, and acrylic chloride (7.75 g) was added thereto dropwise at 0° C., followed by stirring at room temperature for 20 minutes. After completion of the reaction, the organic layer was washed successively with water and a saturated aqueous solution of sodium chloride, and dried over magnesium sulfate. The solvent was removed by evaporation to give 4-fluorophenyl acrylate (13.5 g), which was used in the next reaction without purification.
Physicochemical Properties:
$^1$H-NMR (CDCl$_3$) δ: 5.99 (dd, J=2.43 and 9.81 Hz, 1H), 6.28 (dd, J=9.81 and 16.7 Hz, 1H), 6.62 (dd, J=2.43 and 16.7 Hz, 1H), 7.08 (d, J=5.94 Hz, 4H)
MS (GC/MS): m/z 166 (M$^+$)

(ii) 4-Fluorophenyl acrylate (12.0 g) was added to a mixture of aluminum chloride (33.7 g) and sodium chloride (14.8 g), and the mixture was stirred at 80° C. for 2 hours and then at 160° C. for 1 hour. After completion of the reaction, ice-water and concentrated hydrochloric acid were added, and the reaction mixture was extracted with chloroform. The extract was washed with a saturated aqueous solution of sodium chloride and dried over magnesium sulfate. The solvent was evaporated, and the resulting residue was purified by silica gel column chromatography. From the eluate of hexane-ethyl acetate (9:1), 4-fluoro-7-hydroxy-1-indanone (5.75 g) was obtained as a pale yellow powder.

Physicochemical Properties:

$^1$H-NMR (CDCl$_3$) δ: 2.68–2.82 (m, 2H), 3.08–3.20 (m, 2H), 6.73 (dd, J=3.06 and 8.91 Hz, 1H), 7.13 (d, J=8.91 Hz, 1H), 8.79 (s, 1H)

MS (GC/MS): m/z 166 (M$^+$)

(iii) 4-Fluoro-7-hydroxy-1-indanone (1.0 g) was dissolved in acetic acid (15 ml) and the solution was stirred with 10% palladium-on-carbon (0.5 g) in a hydrogen atmosphere at atmospheric pressure for 12 hours. The catalyst used was removed by filtration using Celite, and the filtrate was concentrated to give 7-fluoro-4-indanol (0.783 g).

Physicochemical Properties:

$^1$H-NMR (CDCl$_3$) δ: 1.95–2.32 (m, 2H), 2.75–3.10 (m, 4H), 4.55 (brs, 1H), 6.54 (dd, J=4.05 and 8.46 Hz, 1H), 8.46 (t, J=8.46 Hz, 1H)

MS (GC/MS): m/z 152 (M$^+$)

EXAMPLE 1

(i) 7-Fluoro-4-indanol (0.30 g) was dissolved in an aqueous solution (5 ml) of potassium hydroxide (0.157 g), and the solution was stirred at room temperature for 1 hour. After the reaction, the solvent was evaporated. 2-p-Toluenesulfonyloxymethyl-4-tritylmorpholine (1.69 g) was added to a dimethylformamide solution (20 ml) of the resulting residue, followed by stirring at 105° C. for 12 hours. After completion of the reaction, a saturated aqueous solution of sodium hydrogencarbonate was added under ice-cooling, and the reaction mixture was extracted with chloroform. The extract was washed with a saturated aqueous sodium chloride solution (100 ml) and dried over magnesium sulfate. The solvent was removed by evaporation, and the residue was purified by silica gel column chromatography. From the hexane-ethyl acetate (9:1) eluate, 2-[[(7-fluoro-4-indanyl)oxy]methyl]-4-tritylmorpholine (0.54 g) was obtained.

Physicochemical Properties:

$^1$H-NMR (CDCl$_3$) δ: 1.40–2.25 (m, 2H), 2.60–3.20 (m, 6H), 3.75–4.05 (m, 5H), 6.50–7.65 (m, 17H)

MS (FAB/pos.): m/z 494 (M$^+$+1)

(ii) To 20 ml of a methanalic solution of 0.54 g of 2-[[(7-fluoro-4-indanyl)oxy]methyl]-4-tritylmorpholine was added a methanolic solution (5 ml) of concentrated hydrochloric acid (1.30 g, 12.8 mmol) at room temperature, followed by stirring for 30 minutes. After completion of the reaction, the reaction mixture was neutralized with a saturated aqueous solution of sodium hydrogencarbonate. The solvent was evaporated, and a saturated aqueous sodium chloride solution was added to the resulting residue, followed by extraction with chloroform. The extract was washed with a saturated aqueous sodium chloride solution and dried over magnesium sulfate. The solvent was evaporated, and the resulting residue was purified by silica gel column chromatography to obtain 2-[[(7-fluoro-4-indanyl)oxy]methyl]morpholine (0.236 g) as a colorless oily substance from the chloroform-methanol-concentrated ammonia (10:1:0.1) eluate.

Physicochemical Properties:

$^1$H-NMR (CDCl$_3$) δ: 1.90–2.28 (m, 2H), 2.55–3.17 (m, 8H), 3.50–4.04 (m, 5H), 6.56 (dd, J=4.23 and 8.55 Hz, 1H), 6.76 (t, J=8.55 Hz, 1H)

MS (GC/MS): m/z 251 (M$^+$)

The above-obtained 2-[[(7-fluoro-4-indanyl)oxy]methyl]morpholine was converted to a hydrochloride, which was recrystallized from methanol-diethyl ether-isopropyl ether to give white crystals.

Physicochemical Properties:

m.p.: 169°–171° C.

$^1$H-NMR (CDCl$_3$) δ: 2.06 (quint., J=7.6 Hz, 2H), 2.78–3.02 (m, 5H), 3.15–3.36 (m, 3H), 3.81 (dt, J=2.0 Hz and 10.0 Hz, 1H), 3.90–4.25 (m, 4H), 6.76 (dd, J=3.60 and 8.80 Hz, 1H), 6.90 (t, J=8.80 Hz, 1H)

MS (GC/MS): m/z 251 (M$^+$)

Elemental analysis for $C_{14}H_{18}NO_2F \cdot HCl \cdot 0.2H_2O$:

|  | C | H | N | Cl | F |
|---|---|---|---|---|---|
| Calcd. (%): | 57.71 | 6.71 | 4.81 | 12.17 | 6.52 |
| Found (%): | 57.77 | 6.67 | 4.71 | 12.44 | 6.50 |

EXAMPLE 2

(i) In the same manner as in Example 1-(i), except for using 7-chloro-4-indanol (0.300 g), 2-[[(7-chloro-4-indanyl)oxy]methyl]-4-tritylmorpholine (0.790 g) was obtained as a pale yellow powder.

Physicochemical Properties of 2-[[(7-Chloro-4-indanyl)oxy]methyl]-4-tritylmorpholine:

$^1$H-NMR (CDCl$_3$) δ: 1.25–2.23 (m, 6H), 2.66–3.18 (m, 4H), 3.72–4.31 (m, 5H), 6.55 (d, J=9.00 Hz, 1H), 7.04 (d, J=9.00 Hz, 1H), 7.12–7.65 (m, 15H)

MS (FAB/pos.): m/z 522 [(M+1)$^+$]

(ii) In the same manner as in Example 1-(ii), except for using 2-[[(7-chloro-4-indanyl)oxy]methyl]-4-tritylmorpholine (0.55 g), 2-[[(7-chloro-4-indanyl)oxy]methyl]morpholine hydrochloride (0.252 g) was obtained as a pale yellow oily substance.

Physicochemical Properties:

$^1$H-NMR (CDCl$_3$) δ: 1.95–2.28 (m, 4H), 2.85–3.10 (m, 6H), 3.50–4.15 (m, 5H), 6.59 (d, J=8.64 Hz, 1H), 7.06 (d, J=8.64 Hz, 1H)

MS (EI): m/z 267 (M+), 269 [(M+2)$^+$]

EXAMPLE 3

To 72.3 g of 7-fluoro-4-indanol was added an aqueous solution of potassium hydroxide (potassium hydroxide: 72.3 g; water: 150 ml), followed by stirring until the indanol was dissolved. To the solution was added 40.8 ml of (R)-(−)-epichlorohydrin, followed by stirring for 8 hours. To the reaction mixture was added 1 l of water, and the mixture was extracted with three 1 l portions of ethyl ether. The ethyl ether solution was dried over anhydrous magnesium sulfate and concentrated under reduced pressure to give 97 g of an oily substance.

To 670.4 g of aminoethylsulfuric acid was added an aqueous solution of potassium hydroxide (potassium hydroxide: 313.5 g; water: 188 ml), and subsequently the above-obtained oily substance dissolved in 600 ml of methanol was added thereto. The mixture was stirred at 50° C. for 4 hours, and an aqueous solution of potassium hydroxide (potassium hydroxide: 627 g; water: 380 ml) was added thereto, followed by further stirring at 50° C. for 18 hours. To the reaction mixture were added 2 l of water and 2 l of ethyl ether. Any insoluble matter was removed by filtration, and the filtrate was extracted with three 2 l portions of ethyl ether. The ethyl ether solution was dried over anhydrous magnesium sulfate and concentrated under reduced pressure to obtain 114 g of an oily substance.

D-Dibenzoyltartaric acid was dissolved in a mixed solvent of 1 l of acetonitrile and 1.3 l of water, and the above-obtained oily substance dissolved in 0.5 l of acetonitrile was added thereto while heating under reflux. After heat-refluxing for 1 hour, the reaction mixture was cooled while stirring in an ice bath. The precipitated salt was collected by filtration, washed with acetonitrile, and dried to give 140 g of (−)-2-[[(7-fluoro-4-indanyl)oxy]methyl]morpholine D-dibenzoyltartrate having an optical purity of 99.9% e.e.

Physicochemical Properties:

$^1$H-NMR (DMSO) δ: 2.09 (tt, J=7.2 Hz, 2H), 2.76 (t, J=7.6 Hz, 2H), 2.81–2.94 (m, 6H), 3.09 (d, J=12.4 Hz, 1H), 3.21 (d, J=12.4 Hz, 1H), 3.64–3.69 (m, 1H), 3.84–3.95 (m, 4H), 5.65 (s, 2H), 6.69 (dd, J=3.6 Hz, J=8.8 Hz, 1H), 6.89 (dd, J=8.8 Hz, 1H), 7.51 (dd, J=7.2 Hz, 4H), 7.64 (dd, J=8 Hz, 2H), 7.97 (d, J=7.6 Hz, 4H)

MS (FAB/pos.): m/z 252 (M+1)$^+$

EXAMPLE 4

To 10 g of (−)-2-[[(7-fluoro-4-indanyl)oxy]methyl]morpholine D-dibenzoyltartrate was added an aqueous solution of sodium hydroxide (sodium hydroxide: 4 g; water: 200 ml), and the mixture was extracted with three 200 ml portions of methylene chloride. The organic layer was dried over anhydrous magnesium sulfate and concentrated under reduced pressure. To the residue were added 1.91 g of fumaric acid and 110 ml of 2-propanol, and the mixture was heated until complete dissolution. The solution was cooled in an ice bath, and the precipitated salt was collected by filtration, washed with 2-propanol, and dried to give 5.04 g of (−)-2-[[(7-fluoro-4-indanyl)oxy]methyl]morpholine fumarate having an optical purity of 99.9% e.e.

Physicochemical Properties:
m.p.: 141°–142° C.

| Elemental analysis for $C_{18}H_{22}NO_6F$: | | | | |
|---|---|---|---|---|
| | C | H | N | F |
| Calcd. (%): | 58.85 | 6.04 | 3.81 | 5.17 |
| Found (%): | 58.85 | 6.07 | 3.84 | 5.23 |

$^1$H-NMR (DMSO) δ: 2.05 (tt, J=7.6 Hz, 2H), 2.75–2.89 (m, 8H), 3.00 (d, J=12.4 Hz, 1H), 3.16 (d, J=12.4 Hz, 1H), 3.63–3.69 (m, 1H), 3.88–4.01 (m, 4H), 6.51 (s, 2H), 6.76 (dd, J=3.6 Hz, J=8.8 Hz, 1H), 6.89 (dd, J=8.8 Hz, 1H)

MS (GC/MS): m/z 251 (M)$^+$

EXAMPLE 5

To 107 g of (−)-2-[[(7-fluoro-4-indanyl)oxy]methyl]morpholine D-dibenzoyltartrate was added an aqueous solution of sodium hydroxide (sodium hydroxide: 21 g; water: 1 l), and the mixture was extracted with three 500 ml portions of ethyl ether. The organic layer was dried over anhydrous magnesium sulfate, concentrated under reduced pressure, and dissolved in 1.2 l of ethyl ether. To the solution was added 53 ml of 4N hydrochloric acid-ethyl acetate. The precipitated salt was collected by filtration, washed with ethyl ether and dried under reduced pressure to give 47.8 g of (−)-2-[[(7-fluoro-4-indanyl)oxy]methyl]morpholine hydrochloride. Physicochemical Properties of (−)-2-[[(7-fluoro-4-indanyl)oxy]methyl]morpholine Hydrochloride:

m.p.: 170°–171° C.

IR (KBr): 1284 cm$^{-1}$, 1492 cm$^{-1}$ $^1$H-NMR (DMSO) δ: 2.05 (tt, J=7.6 Hz, 2H), 2.80–3.00 (m, 8H), 3.19 (d, J=12.4 Hz, 1H), 3.33 (d, J=12.4 Hz, 1H), 3.87 (t, J=10.4 Hz, 1H), 3.98–4.04 (m, 3H), 4.13–4.15 (m, 1H), 6.77 (dd, J=3.6 Hz, J=8.8 Hz, 1H), 6.90 (dd, J=8.8 Hz, 1H)

MS (GC/MS): m/z 251 (M$^+$)

| Elemental analysis for $C_{14}H_{19}NO_2FCl.0.05H_2O$: | | | | | |
|---|---|---|---|---|---|
| | C | H | N | Cl | F |
| Calcd. (%): | 58.25 | 6.67 | 4.85 | 12.28 | 6.58 |
| Found (%): | 58.14 | 6.72 | 4.84 | 12.18 | 6.36 |
| $[α]_D^{20} = −3.00$ | | | | | |

The compound of Example 6 was obtained in the same manner as in Example 1.

EXAMPLE 6

2-[[(6-Fluoro-4-indanyl)oxy]methyl]morpholine fumarate

Starting compound: 6-fluoro-4-indanol
Physicochemical Properties:
m.p.: 173°–174° C.

| Elemental analysis for $C_{18}H_{22}NO_6F$: | | | | |
|---|---|---|---|---|
| | C | H | N | F |
| Calcd. (%): | 58.85 | 6.04 | 3.81 | 5.17 |
| Found (%): | 58.70 | 5.99 | 3.77 | 5.06 |

MS (GC/MS): m/z 251 (M$^+$)

$^1$H-NMR (DMSO) δ: 2.01 (2H, tt, J=7.32 Hz), 2.68–2.73 (3H, m), 2.77–2.85 (3H, m), 2.93 (1H, d, J=12.21 Hz), 3.09 (1H, d, J=11.72 Hz), 3.61 (1H, dt, J=2.44, 11.72 Hz), 3.85–3.88 (2H, m), 3.95–4.03 (2H, m), 6.52 (2H, s), 6.64 (2H, d, J=10.74 Hz)

In the same manner as in Example 2, the compounds of Examples 7 and 8 were obtained.

EXAMPLE 7

2-[[(7-Fluoro-1-methyl-4-indanyl)oxy]methyl]-morpholine hydrobromide

Physicochemical Properties:
MS (m/z): 265 (M)$^+$
IR (KBr) cm$^{-1}$: 1496, 1246
H-NMR (DMSO) δ: 1.23 (d, J=6.8 Hz, 3H), 1.62–1.70 (m, 1H), 2.22–2.31 (m, 1H), 2.70–2.78 (m, 1H), 2.83–3.05 (m, 3H), 3.24 (d, J=12.4 Hz, 1H), 3.33–3.41 (m, 2H), 3.73–3.78 (m, 1H), 4.01–4.03 (m, 4H), 6.77 (dd, J=3.6 Hz, J=8.8 Hz, 1H), 6.90 (dd, J=8.8 Hz, 1H)

EXAMPLE 8

2-[[(7-Fluoro-2-methyl-4-indanyl)oxy]methyl]-morpholine fumarate

Physicochemical Properties:
m.p.: 146°–148° C.
MS (m/z): 265 (M$^+$-C$_4$H$_4$O$_4$)

¹H-NMR (DMSO-d₆) δ: 1.18 (3H, d, 7.33 Hz),0 1.64–1.71 (1H, m), 2.20–2.29 (1H, m), 2.60–2.83 (4H, m), 2.89–2.97 (1H, m), 3.00 (1H, d, 12.20 Hz), 3.05–3.70 (5H, m), 3.76–3.83 (2H, m), 3.88–3.97 (2H, m), 6.51 (2H, s), 6.73–6.76 (1H, m), 6.87–6.91 (1H, m)

EXAMPLE 9

(i) In the same manner as in Example 1-(i), except for using 4-fluoro-7-hydroxy-1-indanone and 2-p-toluenesulfonyloxymethyl-4-tritylmorpholine, 2-[[4-(7-fluoro-3-oxyindanyl)oxy]methyl]-4-tritylmorpholine was obtained.

¹H-NMR (CDCl₃) δ: 1.40–1.70 (2H, m), 2.62–2.80 (2H, m), 3.03–3.25 (2H, m), 3.28–3.53 (1H, m), 3.55–3.72 (1H, m), 3.84–4.22 (4H, m), 4.31–4.57 (1H, m), 6.68–6.78 (1H, m), 7.10–7.60 (16H, m)

MS (m/z): 507 (M⁺)

(ii) 2-[[4-(7-Fluoro-3-oxoindanyl)oxy]methyl]-4-tritylmorpholine (507 mg, 1.00 mmol) was dissolved in methanol (30 ml), and sodium borohydride (37.8 mg, 1.00 mmol) was added thereto, followed by stirring at room temperature for 1 hour. After completion of the reaction, the precipitated colorless crystals were collected by filtration to give 2-[[(7-fluoro-3-hydroxy-4-indanyl)oxy]methyl]-4-tritylmorpholine (220 mg). Water was added to the filtrate, the mixture-extracted with chloroform, the extract dried over anhydrous sodium sulfate, and the solvent removed by evaporation under reduced pressure to give 2-[[4-(7-fluoro-3-hydroxy-4-indanyl)oxy]methyl]-4-tritylmorpholine (282 mg) as colorless crystals. The resulting crystals were combined with the previously collected crystals to give 2-[[4-(7-fluoro-3-hydroxy-4-indanyl)oxy]methyl]-4-tritylmorpholine (502 mg, 0.986 mmol, 99%). The product was dissolved in ethanol (100 ml), and concentrated hydrochloric acid (300 ml) was added to the solution, followed by heating under reflux for 1 hour. The reaction mixture was rendered weakly basic by addition of a saturated aqueous solution of sodium hydrogencarbonate, the ethanol removed by evaporation under reduced pressure, and the residue extracted with chloroform. The extract was dried over anhydrous sodium sulfate, and the residue was purified by silica gel column chromatography (chloroform:methanol=10:1) to give 2-[[4-(3-ethoxy-7-fluoro-4-indanyl)oxy]methyl]morpholine (257 mg, 93%) as a colorless oily substance.

MS (m/z): 295 (M⁺)

¹H-NMR (CDCl₃) δ: 1.20 (3H, t, J=7.1 Hz), 1.88 (1H, br, s), 2.13–2.27 (2H, m), 2.50–3.25 (6H, m), 3.35–4.20 (5H, m), 3.60 (2H, q, J=7.1 Hz), 4.49–5.15 (1H, m), 6.62 (1H, dd, J=8.4, 3.8 Hz), 6.83 (1H, dd, J=8.4, 8.4 Hz)

(iii) 2-[[4-(3-Ethoxy-7-fluoro-4-indanyl)oxy]methyl]morpholine (230 mg, 0.824 mmol) was dissolved in 1,4-dioxane (150 ml), and p-toluenesulfonic acid (231 mg, 1.65 mmol) was added thereto, followed by heating at 105° C. for 4 hours with stirring. The reaction was conducted with no condenser equipped with the reactor in order to evaporate ethanol produced, and the loss of the solvent (1,4-dioxane) on evaporation was slowly made up for in order to maintain a constant concentration. After completion of the reaction, sodium hydrogencarbonate was added to the reaction mixture, and the solvent was removed by evaporation under reduced pressure. The residue was dissolved in chloroform, washed with water, and dried over anhydrous sodium sulfate. The solvent was evaporated under reduced pressure, and the residue was purified by silica gel column chromatography (chloroform:methanol=10:1) to give 2-[[(7-fluoro-4-indenyl)oxy]methyl]morpholine (134 mg, 0.526 mmol, 65%) as a pale yellow oily substance. The product was dissolved in a mixed solvent of ethyl ether-methanol, and a methanolic solution of fumaric acid (30 mg, 0,259 mmol) was slowly added thereto dropwise while stirring, followed by further stirring for 30 minutes. The precipitated colorless crystals were collected by filtration to obtain of a mixture of 2-[[(7-fluoro-4-indenyl)oxy]methyl]morpholine ½ fumarate, 2-[[(4-fluoro-7-indenyl)oxy]methyl]morpholine ½ fumarate, and 2-[[(4-fluoro-7-indenyl)oxy]methyl]morpholine ½ fumarate (115 mg, 45% based on the 2-[[4-(3-ethoxy-7-fluoro-4-indanyl)oxy]methyl]morpholine). The production ratio of olefin positional isomers was about 1:1 from ¹H-NMR.

MS (m/z): 249 (M⁺–½C₄H₄O₄)

¹H-NMR (DMSO-d₆) δ: 2.68–2.81 (2H, m), 2.90 (1H, d, 12.2 Hz), 3.10 (1H, d, 12.2 Hz), 3.38–3.41 (1H, m), 3.45–3.49 (1H, m), 3.58–3.64 (1H, m), 3.85–3.88 (2H, m), 3.99–4.08 (2H, m), 6.50 (1H, s), 6.59–6.66 (1H, m), 6.82–7.06 (3H, m)

Elemental analysis for C₁₆H₁₈NO₄F.0.4H₂O:

|  | C | H | N | F |
|---|---|---|---|---|
| Calcd. (%): | 61.13 | 5.77 | 4.31 | 5.79 |
| Found (%): | 61.10 | 6.02 | 4.45 | 6.04 |

EXAMPLE 10

In 10 ml of dried THF was dissolved 320 mg (0.68 mmol) of 2-[[(7-fluoro-3-oxo-4-indanyl)oxy]methyl]-4-tritylmorpholine, and a diethyl ether solution of 1.16M methyllithium (3.27 ml, 3.78 mmol) was added thereto in an alcohol atmosphere at −78° C., followed by stirring for 2 hours. After completion of the reaction, the temperature was raised to room temperature, and a saturated aqueous ammonium chloride solution was added thereto. The mixture was extracted with chloroform, the extract dried over anhydrous sodium sulfate, and the solvent removed by evaporation under reduced pressure. The residue was dissolved in a mixed solvent of ethyl acetate (5 ml) and acetic acid (5 ml), and palladium-on-carbon (500 mg) was added to the solution. The solution was stirred at room temperature for 12 hours in a hydrogen atmosphere.

After completion of the reaction, the insoluble matter was removed by filtration, and the solvent was removed from the filtrate by evaporation under reduced pressure. A 1N aqueous sodium hydroxide solution was added to the residue, and the solution was extracted with chloroform. The extract was dried over anhydrous sodium sulfate, and the solvent was evaporated under reduced pressure. The residue was purified by silica gel column chromatography (chloroform:methanol:aqueous ammonia=20:1:0.1) to obtain 2-[[(7-fluoro-3-methyl-4-indanyl)oxy]methyl]morpholine (73 mg, 0.28 mmol, 44%) as a pale brown oily substance. The product was dissolved in a mixed solvent of ethyl ether and methanol, and a methanolic solution of fumaric acid (15 mg, 0.129 mmol) was slowly added thereto while stirring. The precipitate was collected by filtration to obtain 2-[[(7-fluoro-3-methyl-4-indanyl)oxy]methyl]morpholine fumarate (66 mg, 33% based on 2-[[(7-fluoro-3-oxo-4-indanyl)oxy]methyl]-4-tritylmorpholine) as colorless crystals.

m.p.: 133°–134° C., 143°–144° C.

MS (m/z): 265 (M⁺–½C₄H₄O₄)

¹H-NMR (DMSO-d₆) δ: 1.19 (3H, d, 7.33 Hz), 1.64–1.72 (1H, m), 2.19–2.29 (1H, m), 2.62–3.04 (6H, m), 3.30 (1H, bs), 3.53–3.59 (1H, m), 3.73–3.88 (2H, m), 3.88–4.00 (2H, m), 6.49 (1H, s), 6.73–6.76 (1H, m), 6.89–6.91 (1H, m)

Elemental analysis for $C_{17}H_{22}NO_4F$:

|  | C | H | N | F |
|---|---|---|---|---|
| Calcd. (%): | 62.99 | 6.78 | 4.26 | 5.63 |
| Found (%): | 63.14 | 6.86 | 4.33 | 5.88 |

EXAMPLE 11

To 180 mg of 2-[[(7-fluoro-4-indanyl)oxy]methyl]morpholine were added 1 ml of a 35% aqueous formaldehyde solution and 1 ml of formic acid, and the mixture was stirred at 80° C. for 7 hours, followed by concentration under reduced pressure. The concentrate was neutralized by addition of 20 ml of a saturated aqueous solution of sodium hydrogencarbonate. The mixture was extracted with three 20 ml portions of ethyl ether. The ethyl ether solution was dried over anhydrous magnesium sulfate and concentrated under reduced pressure. The resulting oil was dissolved in 20 ml of ethyl ether, and a solution of 42 mg of fumaric acid in 1 ml of methanol was added thereto while stirring. The precipitated salt was collected by filtration, washed with ethyl ether, and dried to give 123 mg of 4-methyl-2-[[(7-fluoro-4-indanyl)oxy]methyl]morpholine fumarate.

m.p.: 157°–159° C.

Elemental analysis for $C_{19}H_{24}NO_6F$:

|  | C | H | N |
|---|---|---|---|
| Calcd. (%): | 59.63 | 6.34 | 3.67 |
| Found (%): | 59.63 | 6.31 | 3.69 |

EXAMPLE 12

In 3 ml of acetone was dissolved 220 mg of 2-[[(7-fluoro-4-indanyl)oxy]methyl]morpholine, and 121 mg of potassium carbonate and 70 µl of ethyl iodide were added to the solution, followed by reacting by heating under reflux for 3 hours. To the reaction mixture was added 20 ml of water, and the mixture was extracted with three 20 ml portions of chloroform. The chloroform solution was dried over anhydrous magnesium sulfate and concentrated under reduced pressure. The resulting oil was dissolved in 20 ml of ethyl ether, and 260 µl of an ethyl acetate solution of 4N hydrochloric acid was added thereto while stirring. The precipitated salt was collected by filtration, washed with ethyl ether and dried to give 214 mg of 4-ethyl-2-[[(7-fluoro- 4-indanyl)oxy]methyl]morpholine hydrochloride.

m.p.: 199°–201° C.

Elemental analysis for $C_{16}H_{23}NO_2FCl$:

|  | C | H | N | Cl | F |
|---|---|---|---|---|---|
| Calcd. (%): | 60.85 | 7.34 | 4.44 | 11.23 | 6.02 |
| Found (%): | 60.44 | 7.38 | 4.38 | 11.22 | 5.86 |

(Formulation Examples)

Formulation Examples for the compound of the present invention for use as pharmaceuticals are described below. Formulation example of oral preparations of the compound of Example 5:

| Composition | 20 mg Tablet |
|---|---|
| Compound of Example 5 | 20 mg |
| Lactose | 73 mg |
| Corn starch | 18 mg |
| Hydroxypropylcellulose | 4 mg |
| Calcium carboxymethylcellulose | 4 mg |
| Magnesium stearate | 0.8 mg |
| Total | 120 mg |

Tablets each containing 20 mg of the compound of Example 5:

The compound of Example 5 (100 g), lactose (385.5 g), and corn starch (91.5 g) were uniformly mixed by using a fluidized bed granulation coating apparatus (manufactured by Ohkawara Seisakusho), and a 10% aqueous solution of hydroxypropylcellulose (200 g) was sprayed thereon for granulation. After drying, the granules were passed through a 20 mesh sieve, combined with calcium carboxymethylcellulose (20 g) and magnesium stearate (3 g), and tabletted by means of a rotary tabletting machine (manufactured by Hata Tekkosho) using a punch (7 mm×8.4 R) to obtain tablets each weighing 120 mg.

TABLE 2

| Example No. | Chemical Structural Formula |
|---|---|
| 1 | 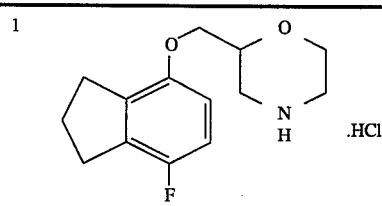 |
| 2 | 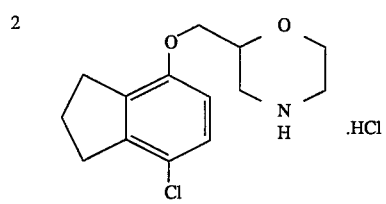 |

TABLE 2-continued

| Example No. | Chemical Structural Formula |
|---|---|
| 3 | 4-fluoro-indanyloxymethyl-morpholine with dibenzoyl tartaric acid (−) Form |
| 4 | 4-fluoro-indanyloxymethyl-morpholine · fumaric acid (−) Form |
| 5 | 4-fluoro-indanyloxymethyl-morpholine · HCl (−) Form |

TABLE 3

| Example No. | Chemical Structural Formula |
|---|---|
| 6 | 6-fluoro-indanyloxymethyl-morpholine · fumaric acid |
| 7 | 1-methyl-4-fluoro-indanyloxymethyl-morpholine · HBr |
| 8 | 2-methyl-4-fluoro-indanyloxymethyl-morpholine · fumaric acid |

TABLE 3-continued

| Example No. | Chemical Structural Formula |
| --- | --- |
| 9 | 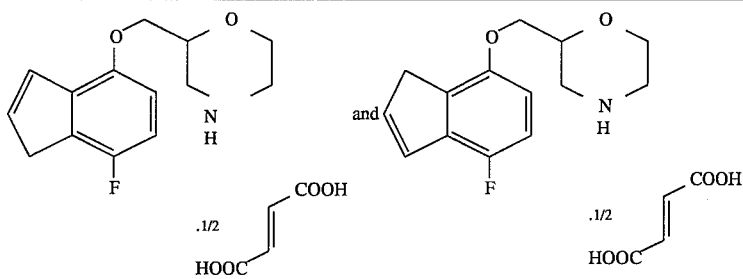 |
| 10 | 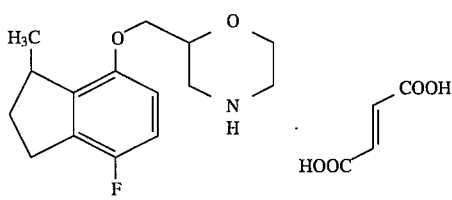 |

TABLE 4

| Example No. | Chemical Structural Formula |
| --- | --- |
| 11 | 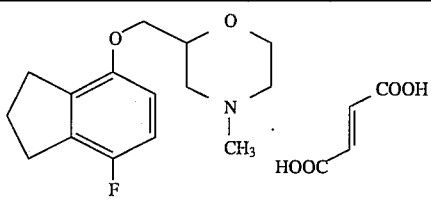 |
| 12 | 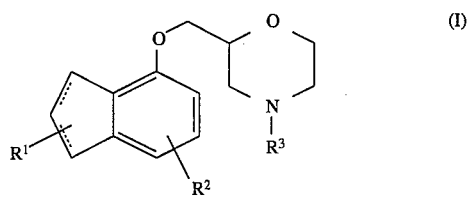 |

We claim:

1. A morpholine derivative represented by formula (I):

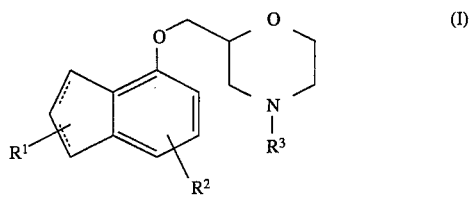

wherein $R^1$ and $R^3$, which may be the same or different, each represent a hydrogen atom or a lower alkyl group; $R^2$ represents a halogen atom; and the dotted line may indicate an optional double bond, or a pharmaceutically acceptable salt thereof.

2. A levorotatory optical isomer of a morpholine derivative represented by formula (I):

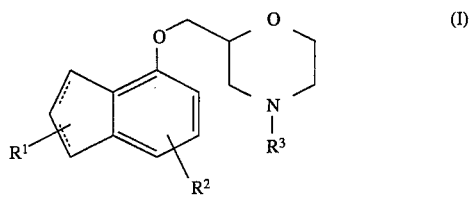

wherein $R^1$ and $R^3$ which may be the same or different, each represent a hydrogen atom or a lower alkyl group; $R^2$ represents a halogen atom; and the dotted line may indicate an optional double bond, or a pharmaceutically acceptable salt thereof.

3. A morpholine derivative represented by formula

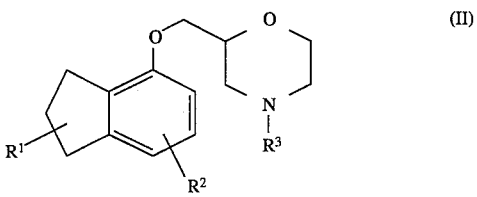

wherein $R^1$ and $R^3$, which may be the same or different, each represent a hydrogen atom or a lower alkyl group; and $R^2$ represents a halogen atom, or a pharmaceutically acceptable salt thereof.

4. A levorotatory optical isomer of a morpholine derivative represented by formula (II):

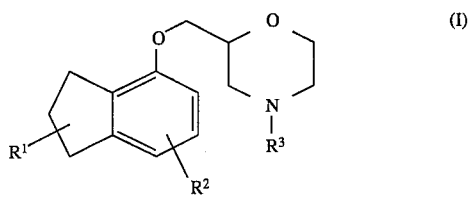

wherein $R^1$ and $R^3$, which may be the same or different, each represent a hydrogen atom or a lower alkyl group; and $R^2$ represents a halogen atom, or a pharmaceutically acceptable salt thereof.

5. 2-[[(7-Fluoro-4-indanyl)oxy]methyl]morpholine or a pharmaceutically acceptable salt thereof.

6. (–)-2-[[(7-Fluoro-4-indanyl)oxy]methyl]morpholine or a pharmaceutically acceptable salt thereof.

7. (31)-2-[[(7-Fluoro-4-indanyl)oxy]methyl]morpholine fumarate.

8. (–)-2-[[(7-Fluoro-4-indanyl)oxy]methyl]morpholine hydrochloride.

9. A method of treating depression or anxiety which comprises administering to a subject as an active ingredient a compound according to any of claims 1 to 8 or a pharmaceutically acceptable salt thereof.

10. A pharmaceutical composition comprising a compound according to any of claims 1 to 8 or a pharmaceutically acceptable salt thereof and a pharmaceutically acceptable carrier.

* * * * *